US00PP32934P2

(12) United States Plant Patent
Van Swieten

(10) Patent No.: US PP32,934 P2
(45) Date of Patent: Mar. 30, 2021

(54) ***PHALAENOPSIS* ORCHID PLANT NAMED 'PHALHALXYP'**

(50) Latin Name: ***Phalaenopsis* hybrid**
Varietal Denomination: PHALHALXYP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/904,829

(22) Filed: Jun. 18, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALHALXYP', particularly characterized by white, striped flowers with red-purple lips, flat flower shape in lateral view, moderately compressed petal shape, and is propagated by meristem tissue culture, is disclosed.

3 Drawing Sheets

Genus and species: *Phalaenopsis* hybrid.
Variety denomination: 'PHALHALXYP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHALXYP'.

The new *Phalaenopsis* plant is a product of a planned breeding program conducted by the inventor in Bleiswijk, the Netherlands. The objective of this breeding program was to create a new *Phalaenopsis* plant with white, striped flowers and red-purple lips, suitable for potted plant production.

The new *Phalaenopsis* plant 'PHALHALXYP' is a result of cross-pollination made by the inventor in July 2010 in Bleiswijk, the Netherlands, of the proprietary female, or seed parent, *Phalaenopsis* hybrid '21396-0002' (unpatented) with the proprietary male, or pollen parent, *Phalaenopsis* hybrid '33408-09' (unpatented).

The new *Phalaenopsis* was selected by the inventor as a single plant within the progeny of the stated cross-pollination in a controlled greenhouse in Bleiswijk, the Netherlands, in July 2013. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 25, 2018 (Application no. 2018/2458), by Applicant who obtained the subject matter disclosed directly from the inventor. 'PHALHALXYP' has not been made publicly available or sold anywhere in the world prior to the effective filing date of this application with the exception of sales or disclosures made one year or less before the effective filing date of this claimed invention by Applicant who obtained 'PHALHALXYP' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHALXYP' as a new and distinct variety of *Phalaenopsis* plant:

1) White, striped flowers with red-purple lips;
2) Flower shape in lateral view is flat; and
3) Petal shape is moderately compressed.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in May 2020. Colors in the photographs may differ from the color values cited in the detailed botanical description, which accurately describe the actual colors of the new variety.

DESCRIPTION OF THE NEW VARIETY

Figure 1:
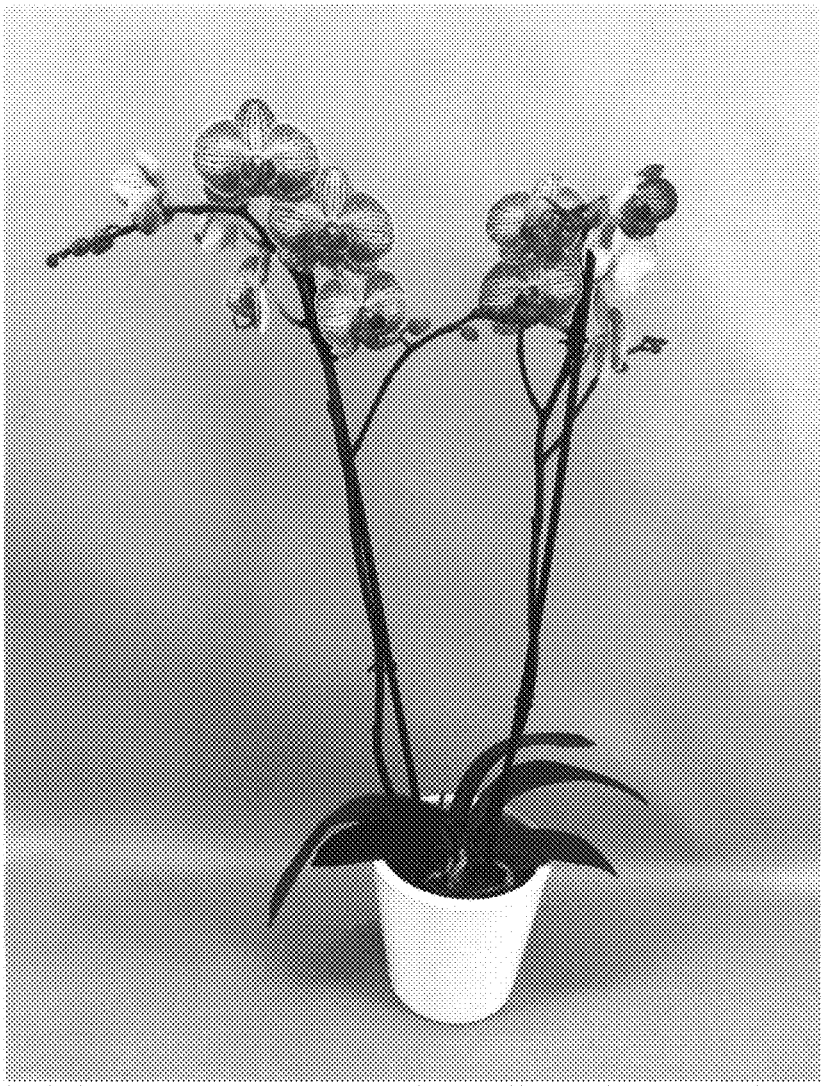
FIG. 1 shows the overall plant habit, including blooms, buds, and foliage of 'PHALHALXYP'.
Figure 2:
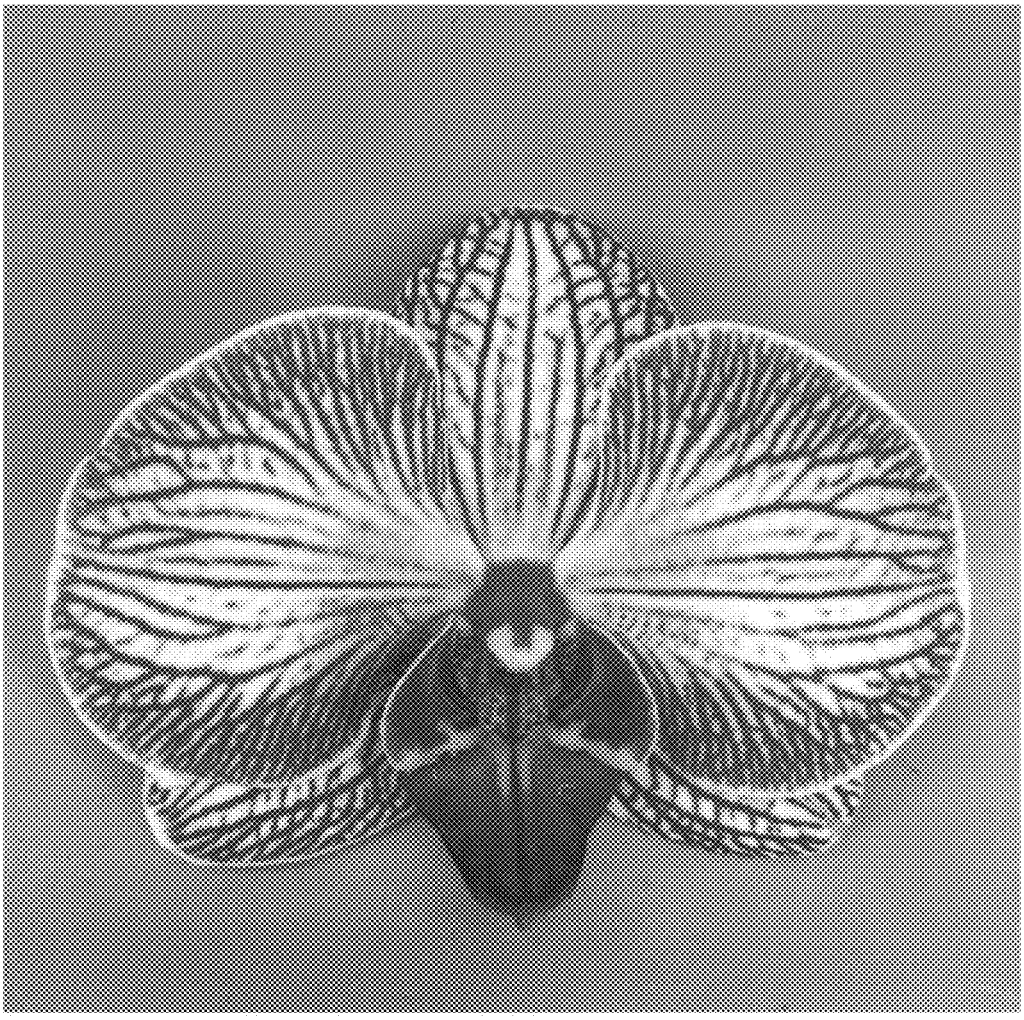
FIG. 2 shows a close-up of a flower of 'PHALHALXYP'.
Figure 3:
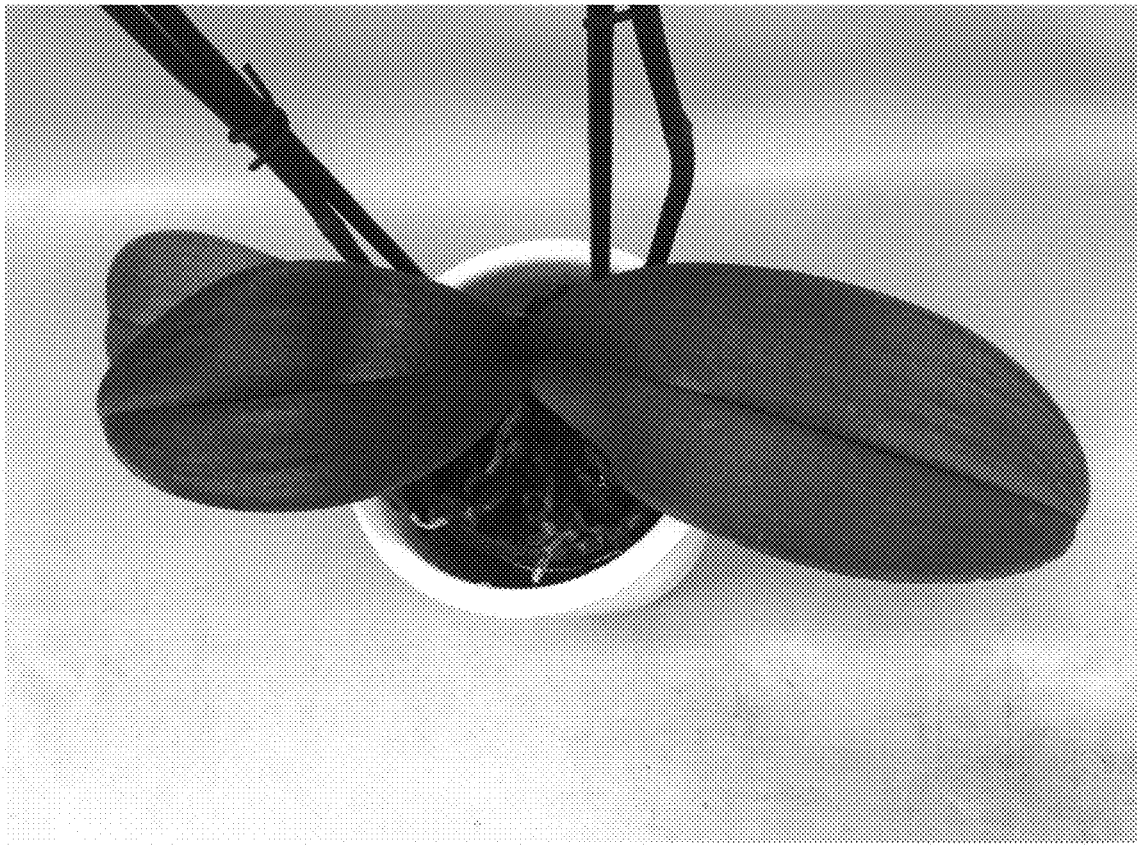
FIG. 3 shows an overhead view of the leaves of 'PHALHALXYP'.

The following detailed description sets forth the distinctive characteristics of 'PHALHALXYP'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in May 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALHALXYP'.

Parentage:

*Female parent*.—*Phalaenopsis* cultivar '21396-0002' (unpatented).

*Male parent*.—*Phalaenopsis* cultivar '33408-09' (unpatented).

Propagation:

*Type*.—Meristem tissue culture.

Roots:

*Root description*.—Greyed-green (something between RHS 190B and 190C) colored roots with branching lateral roots having yellow-green (something in between RHS 145B and 145C) colored root tips.

Plant:

*Commercial crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 59.0 cm to 64.0 cm.

*Width* (*measured from leaf tips*).—About 34.0 cm to 36.0 cm.

*Vigor*.—Strong.

Leaves:

*Mature leaves*.—Quantity per plant: 7 to 9 leaves are produced before flowering. Length (fully expanded): 16.0 cm to 19.0 cm. Width: 7.0 cm to 8.0 cm. Position of the broadest part of the leaf: At the middle. Shape: Oblong. Base shape: Moderately elongated. Apex: Obtuse unequal. Leaf blade angle with the petiole (measured from the horizontal position): Between 20 degrees and 30 degrees. Leaf margin: Entire. Color: Upper surface: RHS 146A. Lower surface: RHS 146B with a hint of RHS 187B. Texture (both upper and lower surfaces): Smooth. Thickness: 2.4 mm to 2.8 mm. Variegation: Absent. Venation: Pattern: Parallel. Color of the midvein: Upper surface: RHS 146A. Lower surface: RHS 187B.

Peduncle:

*Quantity per plant*.—1 to 4.

*Number of flowers per peduncle*.—15 to 18.

*Length*.—59.0 cm to 64.0 cm.

*Diameter*.—5.6 mm to 6.2 mm.

*Strength*.—Strong.

*Aspect*.—Upright to slightly pendent.

*Texture*.—Smooth.

*Color*.—Brown (RHS 200A) with a touch of RHS 146C.

*Internode length*.—3.0 cm to 4.0 cm.

Inflorescence description:

*Appearance*.—Upright to slightly pendent, panicle inflorescence with bilaterally symmetrical flowers that open in succession beginning with the lowermost flower.

*Number of inflorescences*.—1 to 4.

*Inflorescence size*.—Height (from base to tip): 220.0 mm to 290.0 mm.

*Flowering time*.—First flowers can be expected 10 to 11 months after planting in a 12-cm pot.

*Flower*.—Height: 55.0 mm to 60.0 mm. Diameter: 75.0 mm to 80.0 mm. Depth of lip: 23.0 mm to 25.0 mm.

*Flower longevity*.—On the plant: 16 to 18 weeks.

*Flower shape*.—Flat.

*Fragrance*.—Absent.

*Flower bud*.—Average size: Medium. Length: 19.0 mm to 21.0 mm. Width: 16.0 mm to 18.0 mm. Shape: Egg shaped. Color: Light yellow-green (something in between RHS 145B and 145C) with a hint of dark red (RHS 187B).

*Petals*.—Arrangement: Open/free. Shape: Semi-circular. Apex: Emarginated asymmetric. Margin: Weakly undulated. Length (from base to tip): 36.0 mm to 38.0 mm. Width: 42.0 mm to 44.0 mm. Position of the broadest part of the petal: Toward the base. Color (when fully opened): Upper surface: Basic color: White (RHS NN155C). Over color: Light reddish-purple shade (RHS N78D). Lower surface: Basic color: White (RHS NN155C). Over color: Purplish-pink stripes (RHS N78C). Number of spots, dots, and stripes on the petals (upper surface): Many stripes and few very small dots at the base. Color of spots, dots, and stripes on the petals (upper surface): Stripes (RHS N78A) and dots (RHS N78D). Density of netting of the petals (upper surface): None. Color of the netting (upper surface): None.

*Dorsal sepal*.—Shape: Elliptic. Apex: Rounded symmetric. Margin: Entire. Length (from base to tip): 35.0 mm to 37.0 mm. Width: 27.0 mm to 29.0 mm. Position of the broadest part of the dorsal sepals: At the middle. Color (when fully opened): Upper surface: Basic color: White (RHS NN155C). Over color: Light reddish-purple (RHS N78D) at the base. Lower surface: Basic color: White (RHS NN155C). Over color: Very light purple shade (RHS 76B) and diluting reddish-purple stripes (RHS N78B) toward the margin. Number of spots and stripes on the dorsal sepals (upper surface): Medium stripes. Color of spots and stripes on the dorsal sepals (upper surface):

RHS N78A. Density of netting of the dorsal sepals (upper surface): Medium. Color of the netting: RHS N78A.

*Lateral sepals*.—Shape: Ovate. Apex: Obtuse asymmetric. Margin: Entire. Length (from base to tip): 35.0 mm to 37.0 mm. Width: 26.0 mm to 28.0 mm. Position of the broadest part of the lateral sepals: Toward the base. Color (when fully opened): Upper surface: Basic color: White (RHS NN155C). Over color: Absent. Lower surface: Basic color: White (RHS NN155C). Over color: Diluting stripes (RHS N78B) toward the margin. Number of spots, dots, and stripes on the lateral sepals (upper surface): Medium stripes and medium dots (very small dots at the base). Color of spots, dots, and stripes on the lateral sepals (upper surface): Stripes (RHS N78A) and dots (RHS 71A). Density of netting of the lateral sepals (upper surface): Medium. Color of the netting (upper surface): RHS N78A.

*Labellum* (*lip*).—Whiskers: Present. Length of whiskers: 10.0 mm to 12.0 mm. Color of whiskers: Dark purplish-red (RHS N79C) at the base and lighter (RHS N79B) toward the tips; small white tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 17.0 mm to 19.0 mm. Width: 13.0 mm to 15.0 mm. Color: Upper surface: Hint of white (RHS NN155C) at the base; greenish-yellow margin (RHS 6A) on one side; dark red-purple (something in between RHS 187B and N79C); light reddish-purple region (RHS N78D) in the middle and reddish-purple (RHS N78A) toward the margin. Lower surface: White (RHS NN155C) at the base; greenish-yellow margin (RHS 6B) on one side; dark purplish-red stripe (RHS N79C) at base toward the middle and reddish-purple (RHS N78A) toward the margin. Number of spots and stripes on the lateral lobe: Few stripes at the base. Color of spots and stripes on the lateral lobe: RHS 183A. Density of netting of the lateral lobe: None. Color of the netting: None.

*Apical lobe*.—Shape: Triangular. Margin: Entire. Length: 26.0 mm to 28.0 mm. Width: 19.0 mm to 21.0 mm. Color: Upper surface: Hint of greenish-yellow (RHS 6A) at the base; dark red wings (RHS 183A with a touch of RHS 178A); dark purplish red (RHS N79C) with a touch of reddish-purple (RHS N78B) toward whiskers. Lower surface: Purplish-red (RHS N77B) at the base with a touch of light greenish-yellow (RHS 4C); white (RHS NN155C) in the middle; dark red wings (RHS 183A) and dark purplish-red margin (RHS N79C) toward whiskers. Number of spots and stripes on the apical lobe: Few stripes at the base. Color of spots and stripes on the apical lobe: RHS 183A. Density of netting of the apical lobe: None. Color of the netting: None.

*Callus*.—Average size: Medium to large. Height: 5.0 mm to 7.0 mm. Length: 5.0 mm to 6.0 mm. Width: 3.0 mm to 4.0 mm. Color: Yellow (RHS 7A); dotted (RHS 187B).

Reproductive organs:

*Column*.—Length: 8.0 mm to 10.0 mm. Diameter: 5.2 mm to 5.7 mm. Color: Reddish-purple (RHS N78A).

*Pollinia*.—Quantity: 2. Diameter: 9.0 mm to 1.1 mm. Color: Orange (RHS 24A).

*Ovary*.—Length: 11.0 mm to 13.0 mm. Diameter: 2.2 mm to 2.4 mm.

*Pedicel*.—Length: 37.0 mm to 39.0 mm. Diameter: 2.5 mm to 3.0 mm. Texture: Smooth. Color: Dark red fleck (RHS 187A) at the base; yellow-green (RHS 145B) and very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHALXYP' differs from female parent plant '21396-0002' (unpatented) in that 'PHALHALXYP' has a moderately compressed petal shape and emarginated petal apexes, whereas '21396-0002' has a moderately compressed to medium petal shape and rounded petal apexes. Additionally, 'PHALHALXYP' has larger flowers than '21396-0002'.

'PHALHALXYP' differs from male parent plant '33408-09' (unpatented) in that 'PHALHALXYP' has emarginated petal apexes, whereas '33408-09' has obtuse petal apexes. Additionally, 'PHALHALXYP' has larger flowers than '33408-09'.

'PHALHALXYP' is most similar to the commercial *Phalaenopsis* plants named 'PHALBUKAP' (U.S. Plant Pat. No. 25,445) and 'PHALFESFI' (U.S. Plant Pat. No. 31,481). 'PHALHALXYP' differs from the commercial variety 'PHALBUKAP' in that 'PHALHALXYP' has elliptic dorsal sepals and triangular apical lobes, whereas 'PHALBUKAP' has ovate dorsal sepals and obdeltoid apical lobes. Additionally, 'PHALHALXYP' has shorter whiskers than 'PHALBUKAP'.

'PHALHALXYP' differs from the commercial variety 'PHALFESFI' in that 'PHALHALXYP' has emarginated petal apexes, whereas 'PHALFESFI' has obtuse petal apexes. Additionally, 'PHALHALXYP' has smaller flowers and shorter whiskers than 'PHALFESFI'.

I claim:

1. A new and distinct variety of *Phalaenopsis* plant named 'PHALHALXYP', substantially as described and illustrated herein.

* * * * *